(12) United States Patent  (10) Patent No.: US 7,607,557 B2
Shelton, IV et al.  (45) Date of Patent: *Oct. 27, 2009

(54) SURGICAL STAPLING INSTRUMENTS STRUCTURED FOR PUMP-ASSISTED DELIVERY OF MEDICAL AGENTS

(75) Inventors: Frederick E. Shelton, IV, Hillsboro, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 589 days.

This patent is subject to a terminal disclaimer.

(21) Appl. No.: 11/267,383

(22) Filed: Nov. 4, 2005

(65) Prior Publication Data

US 2007/0102452 A1    May 10, 2007

(51) Int. Cl.
*B67D 5/06* (2006.01)
*A61B 17/10* (2006.01)
(52) U.S. Cl. .................. 227/175.1; 227/19; 227/180.1
(58) Field of Classification Search ............... 227/19, 227/175.1
See application file for complete search history.

(56) References Cited

U.S. PATENT DOCUMENTS

| | | | |
|---|---|---|---|
| 2,037,727 A | 4/1936 | Chapelle |
| 3,269,630 A | 8/1966 | Fleischer |
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,819,100 A | 6/1974 | Noiles et al. |
| 3,894,174 A | 7/1975 | Cartun |
| 3,940,844 A | 3/1976 | Colby et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |

(Continued)

FOREIGN PATENT DOCUMENTS

CA    2458946 A1    3/2003

(Continued)

OTHER PUBLICATIONS

European Search Report, Application No. 06255675.8, dated Feb. 19, 2007 (6 pages).

(Continued)

*Primary Examiner*—Brian D Nash

(57) ABSTRACT

A medical agent dispensing system and surgical instruments that employ the medical agent dispensing system are provided. The dispensing system may be structured for use with a surgical severing/stapling instrument structured for severing and stapling tissue. The dispensing system may include at least one storage reservoir structured for storing at least a component of a medical agent and a pump in communication with the storage reservoir; a delivery tube in communication with the pump which is structured to receive a quantity of the medical agent from the storage reservoir during operation of the pump; and, at least one agent tube in communication with the delivery tube which is structured for communication with a least one agent port formed in a staple cartridge or an anvil of the surgical instrument for dispensing the medical agent therethrough.

23 Claims, 15 Drawing Sheets

U.S. PATENT DOCUMENTS

| | | |
|---|---|---|
| 4,475,679 A | 10/1984 | Fleury, Jr. |
| 4,500,024 A | 2/1985 | DiGiovanni et al. |
| 4,520,817 A | 6/1985 | Green |
| 4,522,327 A | 6/1985 | Korthoff et al. |
| 4,526,174 A | 7/1985 | Froehlich |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,629,107 A | 12/1986 | Fedotov et al. |
| 4,671,445 A | 6/1987 | Barker et al. |
| 4,709,120 A | 11/1987 | Pearson |
| 4,715,520 A | 12/1987 | Roehr, Jr. et al. |
| 4,728,020 A | 3/1988 | Green et al. |
| 4,754,909 A | 7/1988 | Barker et al. |
| 4,767,044 A | 8/1988 | Green |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,892,244 A | 1/1990 | Fox et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 5,027,834 A | 7/1991 | Pruitt |
| 5,031,814 A | 7/1991 | Tompkins et al. |
| 5,040,715 A | 8/1991 | Green et al. |
| 5,065,929 A | 11/1991 | Schulze et al. |
| 5,080,556 A | 1/1992 | Carreno |
| 5,104,025 A | 4/1992 | Main et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,137,198 A | 8/1992 | Nobis et al. |
| 5,156,315 A | 10/1992 | Green et al. |
| 5,200,280 A | 4/1993 | Karasa |
| 5,207,697 A | 5/1993 | Carusillo et al. |
| 5,211,649 A | 5/1993 | Kohler et al. |
| 5,221,036 A | 6/1993 | Takase |
| 5,246,156 A | 9/1993 | Rothfuss et al. |
| 5,253,793 A | 10/1993 | Green et al. |
| RE34,519 E | 1/1994 | Fox et al. |
| 5,275,323 A | 1/1994 | Schulze et al. |
| 5,307,976 A | 5/1994 | Olson et al. |
| 5,309,927 A | 5/1994 | Welch |
| 5,318,221 A | 6/1994 | Green et al. |
| 5,332,142 A | 7/1994 | Robinson et al. |
| 5,350,400 A | 9/1994 | Esposito et al. |
| 5,379,933 A | 1/1995 | Green et al. |
| 5,383,880 A | 1/1995 | Hooven |
| 5,389,098 A | 2/1995 | Tsuruta et al. |
| 5,395,033 A | 3/1995 | Byrne et al. |
| 5,397,046 A | 3/1995 | Savage et al. |
| 5,403,312 A | 4/1995 | Yates et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,433,721 A | 7/1995 | Hooven et al. |
| 5,445,304 A | 8/1995 | Plyley et al. |
| 5,456,401 A | 10/1995 | Green et al. |
| 5,462,215 A | 10/1995 | Viola et al. |
| 5,465,895 A | 11/1995 | Knodel et al. |
| 5,465,896 A | 11/1995 | Allen et al. |
| 5,470,006 A | 11/1995 | Rodak |
| 5,472,132 A | 12/1995 | Savage et al. |
| 5,474,566 A | 12/1995 | Alesi et al. |
| 5,480,089 A | 1/1996 | Blewett |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,518,163 A | 5/1996 | Hooven |
| 5,518,164 A | 5/1996 | Hooven |
| 5,522,817 A | 6/1996 | Sander et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,549,628 A | 8/1996 | Cooper et al. |
| 5,553,675 A | 9/1996 | Pitzen et al. |
| 5,554,169 A | 9/1996 | Green et al. |
| 5,562,239 A | 10/1996 | Boiarski et al. |
| 5,562,241 A | 10/1996 | Knodel et al. |
| 5,564,615 A | 10/1996 | Bishop et al. |
| 5,574,431 A | 11/1996 | McKeown et al. |
| 5,575,803 A | 11/1996 | Cooper et al. |
| 5,577,654 A | 11/1996 | Bishop |
| 5,582,611 A | 12/1996 | Tsuruta et al. |
| 5,584,425 A | 12/1996 | Savage et al. |
| 5,586,711 A | 12/1996 | Plyley et al. |
| 5,588,579 A | 12/1996 | Schnut et al. |
| 5,601,224 A | 2/1997 | Bishop et al. |
| 5,607,094 A | 3/1997 | Clark et al. |
| 5,628,446 A | 5/1997 | Geiste et al. |
| 5,630,539 A | 5/1997 | Plyley et al. |
| 5,632,432 A | 5/1997 | Schulze et al. |
| 5,636,779 A | 6/1997 | Palmer |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,662,258 A | 9/1997 | Knodel et al. |
| 5,667,517 A | 9/1997 | Hooven |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,408 A | 12/1997 | Wales et al. |
| 5,704,534 A | 1/1998 | Huitema et al. |
| 5,706,998 A | 1/1998 | Plyley et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,747,953 A | 5/1998 | Philipp |
| 5,752,644 A | 5/1998 | Bolanos et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,796,188 A | 8/1998 | Bays |
| 5,797,536 A | 8/1998 | Smith et al. |

| | | |
|---|---|---|
| 5,797,537 A | 8/1998 | Oberlin et al. |
| 5,797,538 A | 8/1998 | Heaton et al. |
| 5,807,393 A | 9/1998 | Williamson, IV et al. |
| 5,817,093 A | 10/1998 | Williamson, IV et al. |
| 5,823,066 A | 10/1998 | Huitema et al. |
| 5,826,776 A | 10/1998 | Schulze et al. |
| 5,833,690 A | 11/1998 | Yates et al. |
| 5,836,503 A | 11/1998 | Ehrenfels et al. |
| 5,839,639 A | 11/1998 | Sauer et al. |
| 5,843,132 A | 12/1998 | Ilvento |
| 5,865,361 A | 2/1999 | Milliman et al. |
| 5,871,135 A | 2/1999 | Williamson IV et al. |
| 5,878,938 A | 3/1999 | Bittner et al. |
| 5,893,506 A | 4/1999 | Powell |
| 5,894,979 A | 4/1999 | Powell |
| 5,911,353 A | 6/1999 | Bolanos et al. |
| 5,918,791 A | 7/1999 | Sorrentino et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,032,849 A | 3/2000 | Mastri et al. |
| 6,033,427 A * | 3/2000 | Lee .................... 606/213 |
| 6,079,606 A | 6/2000 | Milliman et al. |
| 6,083,234 A | 7/2000 | Nicholas et al. |
| 6,109,500 A | 8/2000 | Alli et al. |
| H1904 H | 10/2000 | Yates et al. |
| 6,126,670 A | 10/2000 | Walker et al. |
| 6,131,789 A | 10/2000 | Schulze et al. |
| 6,155,473 A | 12/2000 | Tompkins et al. |
| 6,156,056 A | 12/2000 | Kearns et al. |
| 6,202,914 B1 | 3/2001 | Geiste et al. |
| 6,223,835 B1 | 5/2001 | Habedank et al. |
| 6,241,139 B1 | 6/2001 | Milliman et al. |
| 6,250,532 B1 | 6/2001 | Green et al. |
| 6,264,087 B1 | 7/2001 | Whitman |
| 6,273,897 B1 | 8/2001 | Dalessandro et al. |
| 6,315,184 B1 | 11/2001 | Whitman |
| 6,320,123 B1 | 11/2001 | Reimers |
| 6,325,810 B1 | 12/2001 | Hamilton et al. |
| 6,330,965 B1 | 12/2001 | Milliman et al. |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,494,896 B1 * | 12/2002 | D'Alessio et al. ........... 606/213 |
| 6,503,257 B2 | 1/2003 | Grant et al. |
| 6,511,468 B1 | 1/2003 | Cragg et al. |
| 6,522,101 B2 | 2/2003 | Malackowski |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,979 B2 | 1/2004 | Whitman |
| 6,695,199 B2 | 2/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,018,390 B2 * | 3/2006 | Turovskiy et al. .......... 606/167 |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,098,794 B2 | 8/2006 | Lindsay et al. |
| 7,108,701 B2 * | 9/2006 | Evens et al. ................. 606/153 |
| 7,140,527 B2 | 11/2006 | Ehrenfels et al. |
| 7,246,734 B2 | 7/2007 | Shelton, IV |
| 7,303,106 B2 | 12/2007 | Milliman et al. |
| 7,328,828 B2 | 2/2008 | Ortiz et al. |
| 7,354,447 B2 | 4/2008 | Shelton, IV et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 2003/0105478 A1 | 6/2003 | Whitman et al. |
| 2003/0130677 A1 | 7/2003 | Whitman et al. |
| 2003/0216778 A1 | 11/2003 | Weadock |
| 2004/0028502 A1 | 2/2004 | Cummins |
| 2004/0094597 A1 | 5/2004 | Whitman et al. |
| 2004/0097987 A1 | 5/2004 | Pugsley et al. |
| 2004/0111081 A1 | 6/2004 | Whitman et al. |
| 2004/0122471 A1 | 6/2004 | Toby et al. |
| 2004/0148010 A1 * | 7/2004 | Rush ....................... 623/1.13 |
| 2004/0167572 A1 | 8/2004 | Roth et al. |
| 2004/0193177 A1 * | 9/2004 | Houghton et al. .......... 606/108 |
| 2004/0222268 A1 | 11/2004 | Bilotti et al. |
| 2004/0232196 A1 | 11/2004 | Shelton, IV et al. |
| 2004/0232199 A1 | 11/2004 | Shelton, IV et al. |
| 2004/0243151 A1 | 12/2004 | Demmy et al. |
| 2004/0243176 A1 | 12/2004 | Hahnen et al. |
| 2005/0006434 A1 | 1/2005 | Wales et al. |
| 2005/0021026 A1 | 1/2005 | Baily |

| | | |
|---|---|---|
| 2005/0023324 A1 | 2/2005 | Doll et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125035 A1* | 6/2005 | Cichocki .................. 606/222 |
| 2005/0131390 A1 | 6/2005 | Heinrich et al. |
| 2005/0143759 A1 | 6/2005 | Kelly |
| 2005/0165415 A1 | 7/2005 | Wales |
| 2005/0173490 A1 | 8/2005 | Shelton, IV |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0274768 A1 | 12/2005 | Cummins et al. |
| 2006/0011699 A1 | 1/2006 | Olson et al. |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0049229 A1 | 3/2006 | Milliman et al. |
| 2006/0087442 A1 | 4/2006 | Smith et al. |
| 2006/0100643 A1 | 5/2006 | Laufer et al. |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0226196 A1 | 10/2006 | Hueil et al. |
| 2007/0023477 A1 | 2/2007 | Whitman et al. |
| 2007/0034668 A1 | 2/2007 | Holsten et al. |
| 2007/0045379 A1 | 3/2007 | Shelton |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IIV et al. |
| 2007/0262116 A1 | 11/2007 | Hueil et al. |
| 2007/0295780 A1 | 12/2007 | Shelton et al. |
| 2008/0021486 A1* | 1/2008 | Oyola et al. .................. 606/169 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 9412228 U | 9/1994 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0639349 A2 | 2/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |

| | | |
|---|---|---|
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0687119 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0603472 B1 | 11/1998 |
| EP | 0878169 A1 | 11/1998 |
| EP | 0760230 B1 | 2/1999 |
| EP | 0537572 B1 | 6/1999 |
| EP | 0552050 B1 | 5/2000 |
| EP | 1 086 713 B1 | 3/2001 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0705570 B1 | 4/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621141 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1300117 B1 | 8/2007 |
| FR | 1112936 A | 3/1956 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/ads/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

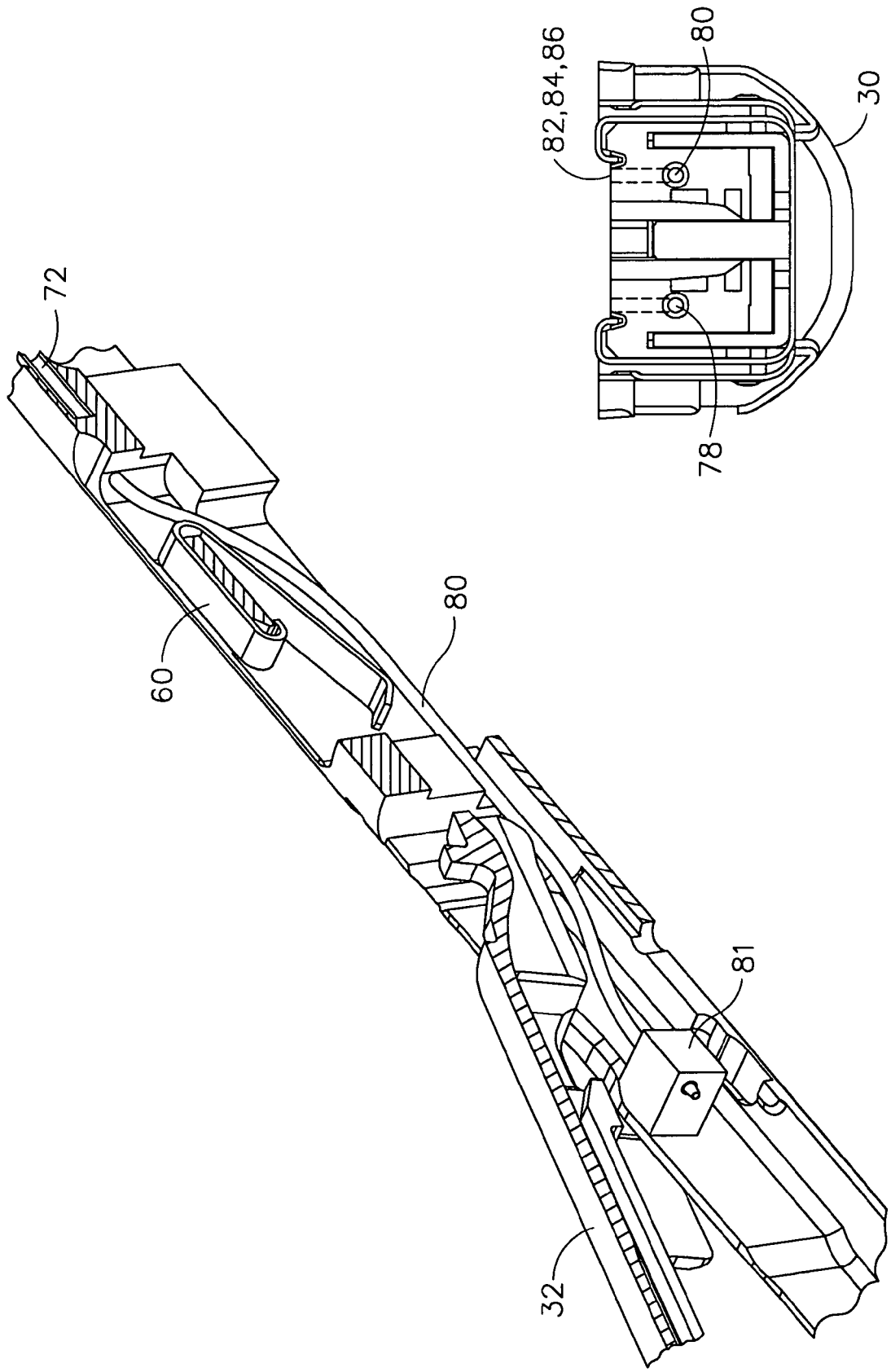

SURGICAL STAPLING INSTRUMENTS STRUCTURED FOR PUMP-ASSISTED DELIVERY OF MEDICAL AGENTS

FIELD OF THE INVENTION

The present invention generally relates to surgical instruments. The invention more particularly relates to delivery and application of medical agents in association with the use of surgical instruments to promote closure and healing of severed and stapled tissue.

BACKGROUND

Conventional surgical staplers that can be used to simultaneously make longitudinal incisions in tissue and apply lines of staples on opposing sides of the incisions are known in the art. Such instruments commonly include a pair of cooperating jaw members that, when employed in endoscopic or laparoscopic applications, are capable of passing through a cannula passageway. One of the jaw members typically receives a staple cartridge having at least two laterally spaced rows of staples. The other jaw member defines an anvil having staple-forming pockets correspondingly aligned with the rows of staples in the cartridge. Such stapling instruments may also include a plurality of reciprocating wedges that pass through openings in the staple cartridge when driven and engage drivers supporting the staples to effect the firing of the staples toward the anvil and through tissue.

Examples of surgical staplers suitable for use with endoscopic applications are described in U.S. Patent Application No. US 2004/0232196 A1. In operation of the surgical stapler, a clinician closes or clamps the jaw members of the stapler on tissue to position the tissue prior to firing or activation of the stapler. Once the clinician has determined that the jaw members are clamping the tissue in a desired position, then the surgical stapler can be fired by the clinician to create an incision in the tissue and at the same time staple tissue surrounding the incision. This simultaneous action of the stapler avoids complications that often arise when the severing and stapling operations are performed sequentially (or at different times) with different surgical tools (i.e., one device is used to sever the tissue, and then another device is used to staple the tissue).

In general, application of certain medical agents to tissue incisions can promote healing, reduce the possibility of infection, and/or promote proper sealing of the incisions. If assisted by the action of such medical agents, many surgical staplers could achieve better surgical results with respect to enhanced healing, improved infection resistance, and improved sealing of tissue incisions. However, the structure of many conventional surgical staplers, and the procedures in which such staplers are employed, do not leverage the benefits of medical agents or systems that dispense medical agents.

In view of the foregoing, there is a need for improved surgical instruments and medical agent dispensing systems than can more effectively and efficiently promote closure, treatment, and healing of tissue incisions severed and stapled during operations involving surgical staplers.

SUMMARY

In accordance with the present invention, various embodiments of a medical agent dispensing system can be provided. The dispensing system may be structured for use with a surgical severing/stapling instrument structured for severing and stapling tissue. The dispensing system may include at least one storage reservoir structured for storing at least a component of a medical agent, and a pump in communication with the storage reservoir. Also, a delivery tube may be in communication with the pump which is structured to receive a quantity of the medical agent from the storage reservoir during operation of the pump. The dispensing system may also include at least one agent tube in communication with the delivery tube which is structured for communication with a least one agent port formed in a staple cartridge of the surgical instrument for dispensing the medical agent therethrough.

In certain embodiments of the invention, a medical agent dispensing system may be provided that includes at least one storage reservoir structured for storing at least a component of a medical agent, and a pump in communication with the storage reservoir. Also, a delivery tube may be in communication with the pump which is structured to receive a quantity of the medical agent from the storage reservoir during operation of the pump. The dispensing system may also include at least one agent tube in communication with the delivery tube which is structured for communication with a least one agent port formed in an anvil of the surgical instrument for dispensing the medical agent therethrough.

In various embodiments of the invention, a surgical severing/stapling instrument may be provided that includes a medical agent dispensing system. The instrument may include a handle portion including at least one storage reservoir structured for storing at least a component of a medical agent. The handle portion may further include a pump in communication with the storage reservoir. The instrument may also include a shaft portion connected to the handle portion that includes a delivery tube in communication with the storage reservoir, such that a medical agent is deliverable from the storage reservoir to the delivery tube during operation of the pump. The instrument may further include an end effector portion operatively associated with the shaft portion, and the end effector may include a channel having a staple cartridge positioned removably therein. The dispensing system may also include at least one agent tube in communication with the delivery tube that extends from the shaft portion to communicate with a least one agent port formed in the staple cartridge for dispensing the medical agent therethrough.

In certain embodiments of the invention, a surgical severing/stapling instrument may be provided that includes a medical agent dispensing system. The instrument may include a handle portion with at least one storage reservoir structured for storing at least a component of a medical agent and a pump in communication with the storage reservoir. The instrument may further include a shaft portion connected to the handle portion. The shaft portion may include a delivery tube in communication with the storage reservoir, such that a medical agent is deliverable from the storage reservoir to the delivery tube during operation of the pump. The instrument may also include an end effector portion operatively associated with the shaft portion, wherein the end effector portion has an anvil. The dispensing system may include at least one agent tube in communication with the delivery tube that extends from the shaft portion to communicate with a least one agent port formed in the anvil for dispensing the medical agent therethrough.

BRIEF DESCRIPTION OF THE FIGURES

The accompanying drawings, which are incorporated into and constitute a part of this specification, illustrate embodiments of the invention. Together with the description of the embodiments provided herein, the drawings serve to explain the principles of the present invention for those skilled in the art.

FIG. 5 includes an enlarged three-dimensional view of portions of the shaft and handle portion of the surgical instrument of FIG. 3;

FIG. 6 includes an end view of the channel of the surgical instrument of FIG. 2;

DESCRIPTION

Figure 1:
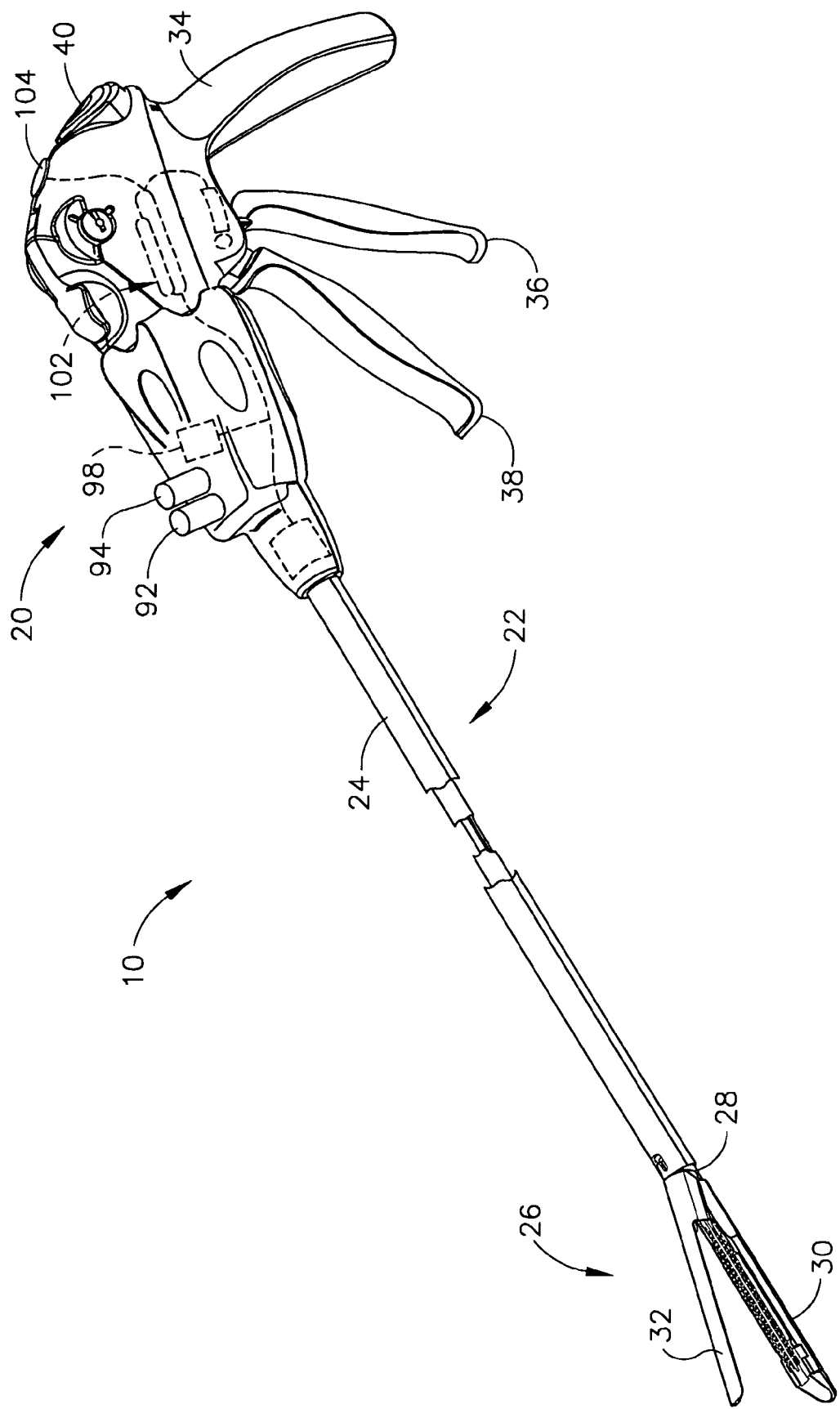
FIG. 1 depicts an three-dimensional, partially cut-away, partially schematic view of a surgical instrument that may be provided in association with embodiments of a medical agent dispensing system in accordance with the present invention.
Figure 2:
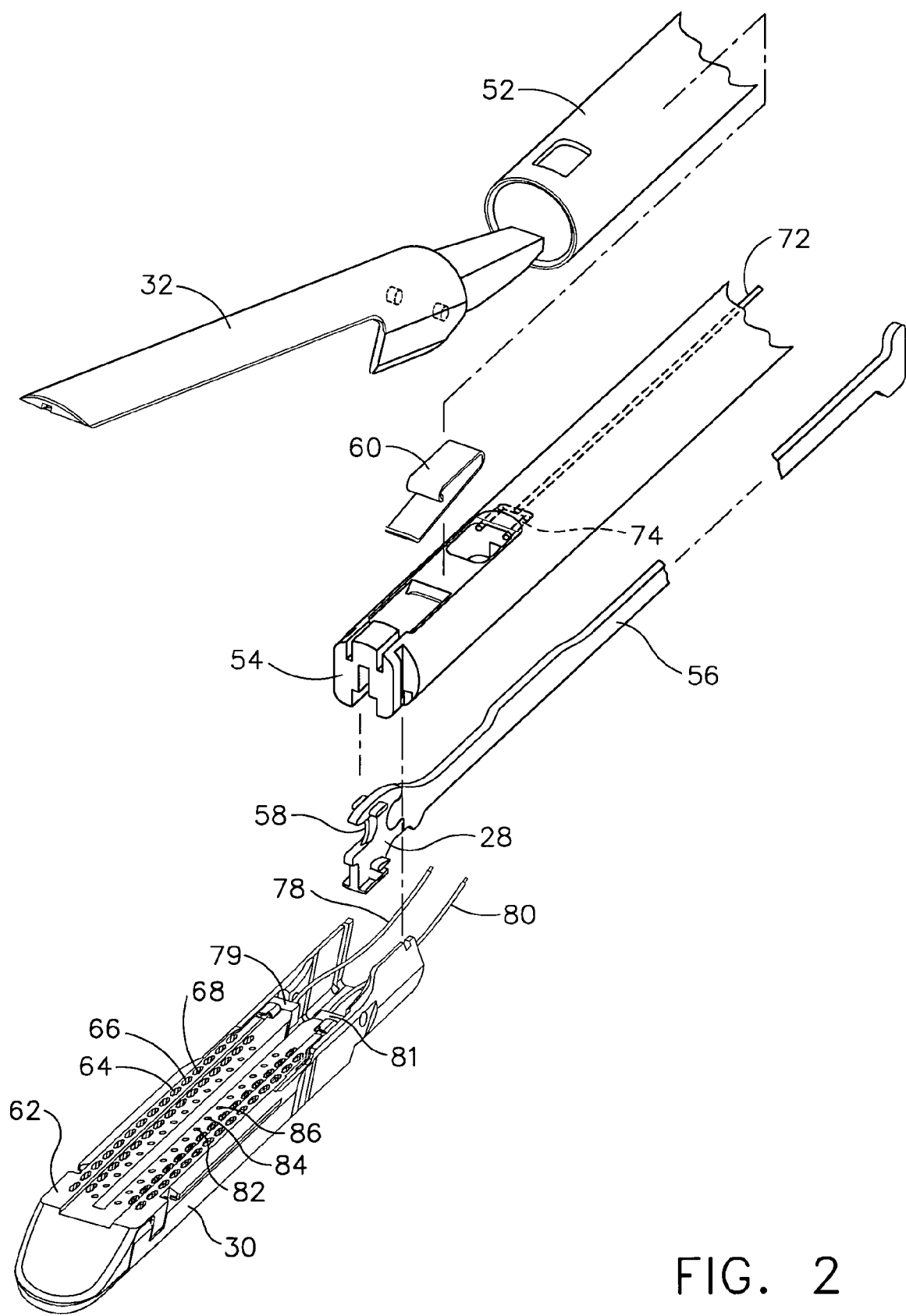
FIG. 2 illustrates a disassembled, three-dimensional view of the end effector and a shaft portion of the surgical instrument of FIG. 1.
Figure 3:
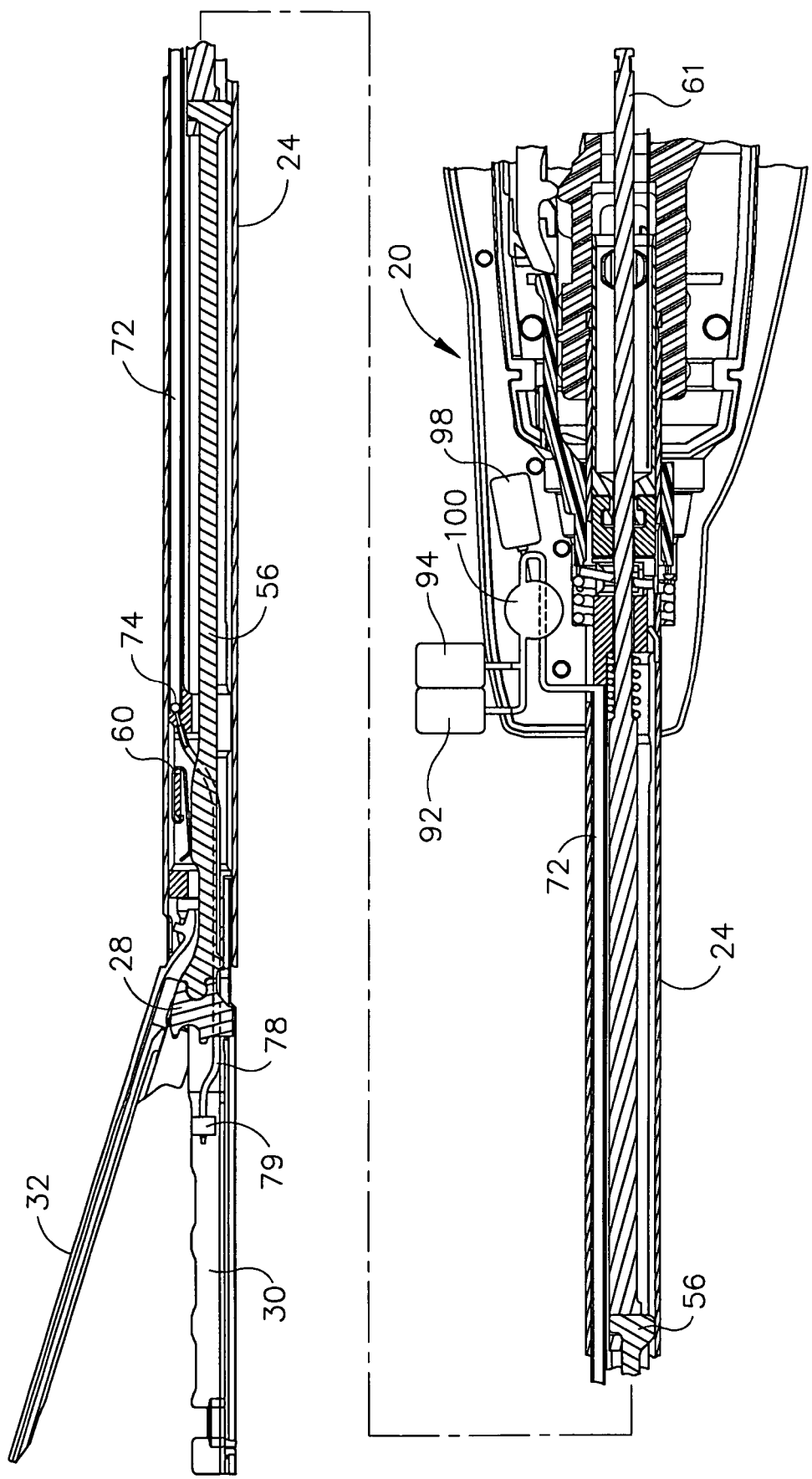
FIG. 3 includes schematic depictions of handle, shaft and end effector portions of the surgical instrument of FIG. 1.

As applied herein, the term "tissue" may include a variety of human or animal tissues, membranes, or other organic substrates. The term "tissue" may also include any substance, substrate, or composition of matter capable of being severed and stapled by the various embodiments of surgical stapling/severing instruments described herein.

As applied herein, the term "medical agent" may include a variety of liquid chemicals, or other compositions of matter in liquid form that may be applied to tissues. Examples of "medical agents" may include, without limitation, hemostatic agents, healing agents, adhesives, sealants, antibacterial agents, infection-resistant agents, analgesics, and various other kinds of medicinal or beneficial substances.

With general reference to FIGS. 1 through 6, in association with various embodiments of the invention, a surgical severing/stapling instrument 10 may be structured with a handle portion 20 connected to an implement portion 22. The implement portion 22 may include a shaft 24 which extends distally from the handle portion 20 and terminates in an end effector 26. The end effector 26 may include an actuator or E-beam firing mechanism ("firing bar") 28 that controls spacing between an elongated channel 30 and a pivotally translatable anvil 32 included within the end effector 26. It can be seen that the spacing between the channel 30 and the anvil 32 may be configured to promote effective stapling and severing of tissue during use of the surgical instrument 10 by a clinician, for example.

The handle portion 20 of the instrument 10 may include a pistol grip 34 toward which a closure trigger 36 may be pivotally drawn by the clinician, for example, to cause clamping or closing of the anvil 32 toward the channel 30 of the end effector 26. In operation, the tissue of a patient, for example, may be clamped by the closing of the anvil 32 toward the channel 30. A firing trigger 38 positioned adjacent to the closure trigger 36 can be pivotally drawn in the direction of the pistol grip 34 to substantially simultaneously staple and sever tissue clamped in the end effector 26 of the instrument 10. In a surgical operation, the clinician first activates the closure trigger 36 to clamp the tissue of a patient, for example. Once the clinician is satisfied with the positioning of the end effector 26, the closure trigger 36 may be drawn back to a fully closed and locked position proximate to the pistol grip 34. The firing trigger 38 of the instrument 10 may then be actuated to sever and staple the clamped tissue. The firing trigger 38 may springedly return to a normal, inactivated state when the clinician removes pressure applied to the firing trigger 38. A release button 40 positioned on the proximal end of the handle portion 20 may be pressed by the clinician to release the locked closure trigger 36 to its normally open position (as shown in FIG. 1).

In various embodiments, the distal end of the shaft 24 may include a closure tube 52 structured to receive and contain portions of the components of the end effector 26, such as the anvil 32 and the channel 30. The closure tube 52 may also be structured to receive a spine 54 extending therethrough that supports a knife shaft 56 having a distally positioned severing edge 58. The knife shaft 56 may operatively interact with the firing bar 28 at the severing edge 58 of the knife shaft 56. A knife spring 60 may be inserted within the spine 54 and structured with a resilient downward bias that promotes proper and secure positioning of the knife shaft 56 within the spine 54. In operation, when the instrument 10 is fired, the knife shaft 56 and its severing edge 58 are moved through the channel 30 by a knife rod 61 to sever tissue clamped between the anvil 32 and the channel 30. The channel 30 may be structured to receive a removable staple cartridge 62 therein. The staple cartridge 62 may have multiple staple holes (such as illustratively representative staple holes 64, 66, 68) formed therein and through which multiple staples (not shown) may be driven to staple severed tissue when the instrument 10 is fired. In certain embodiments, the staple cartridge 62 may be an "ETS45" or "ETS60" six-row cartridge, for example, marketed by Ethicon Endo-Surgery, Inc., of Cincinnati, Ohio.

Examples of the structure and operation of typical surgical stapling instruments that may be provided in association with embodiments of the present invention are disclosed in a United States published patent application to Shelton et al. entitled, "Surgical Stapling Instrument having Separate Distinct Closing and Firing Systems" (U.S. Pub. No. 2004/

0232196, Ser. No. 10/441,632, filed on May 20, 2003), the entirety of which is hereby incorporated by reference.

Figure 4:
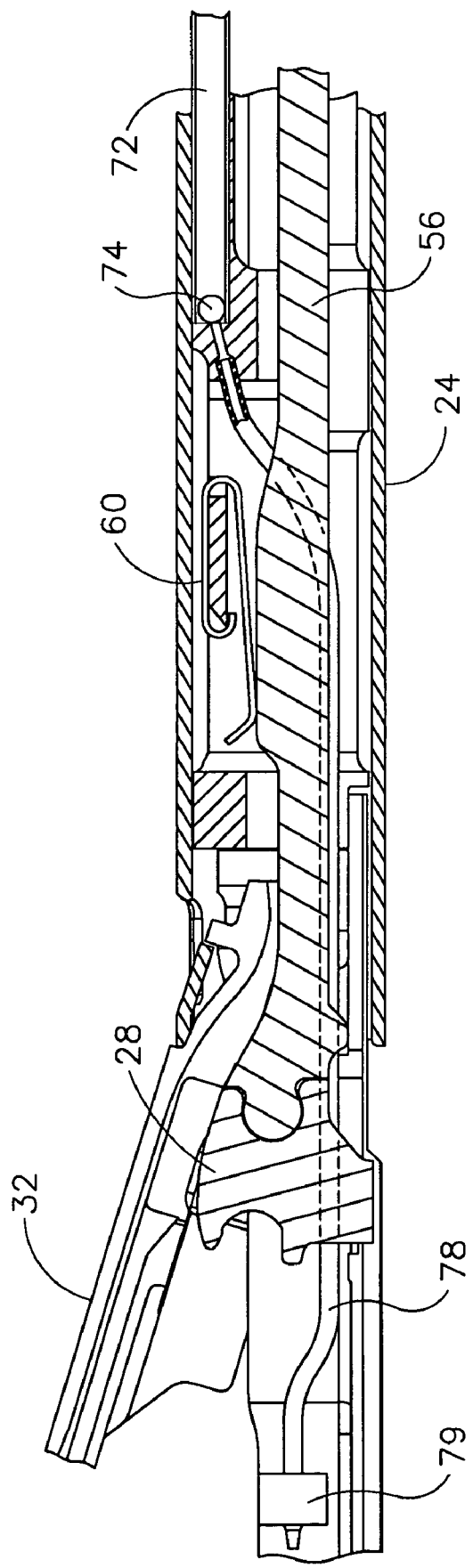
FIG. 4 includes an enlarged view of portions of the shaft and end effector of the surgical instrument of FIG. 3.

With regard to embodiments of a medical agent dispensing system that may be provided in conjunction with the surgical instrument 10, a delivery tube 72 may be positioned to extend longitudinally through the spine 54, and may extend from the handle portion 20 of the instrument 10 to a lateral manifold 74. One or more agent tubes 78, 80 may be positioned to communicate both with the lateral manifold 74 and with a plurality of agent ports (such as illustratively representative agent ports 82, 84, 86) formed in the staple cartridge 62 generally adjacent to the staple holes 64, 66, 68 of the cartridge 62. The agent tubes 78, 80 may be structured for communication with the agent ports 82, 84, 86 in the staple cartridge 62 as shown in the end view of the cartridge 62 of FIG. 6. While a row of agent ports 82, 84, 86 is shown positioned next to both sides of a longitudinal center line of the channel 30, it can be appreciated that more or less such agent ports 82, 84, 86 may be provided in the cartridge 62. For example, more agent ports 82, 84, 86 may be provided in place of one or more of the staple holes 64, 66, 68 formed in the cartridge 62. In various embodiments, one or more structures such as mounting blocks 79, 81 may be included within the channel 30 to facilitate securement and stability of the agent tubes 78, 80 (respectively) within the instrument 10 (see FIG. 1). Also, it can be seen that the agent tubes 78, 80 (such as the left-hand side agent tube 78, as shown in FIG. 4, for example) may be positioned generally adjacent to the knife shaft 56 as the agent tubes 78, 80 extend longitudinally through the shaft 24.

In various embodiments, the handle portion 20 may include one or more medical agent storage reservoirs 92, 94 mounted on the handle portion 20 and in communication with the delivery tube 72. The storage reservoirs 92, 94 may contain a variety of medical agents, or components thereof, that can be beneficially applied to severed and stapled tissue by action of the dispensing system in connection with use of the surgical instrument 10. While multiple storage reservoirs 92, 94 are depicted on the instrument 10 for convenience of disclosure, certain embodiments of the invention may employ only a single storage reservoir, for example, or more than two storage reservoirs. It can be seen that employing multiple storage reservoirs 92, 94 can facilitate real-time mixing of multiple-component medical agents during operation of the medical agent dispensing system. For example, the use of multiple storage reservoirs 92, 94 facilitates combination and use of two-part liquid adhesives, for example, in connection with operation of the dispensing system within the instrument 10. In certain embodiments, the medical agents stored in the storage reservoirs 92, 94 may be the same type of medical agent or different types of medical agents.

Also, in various embodiments of the medical agent dispensing system of the present invention, an electric motor 98 may be included within the handle portion 20 and operatively associated with a pump 100 configured to be driven by the motor 98. Those skilled in the art will appreciate that the electric motor 98 may be any conventional battery-driven or AC-powered motor provided with specifications (e.g., a motor rating) suitable for safe and effective use of the motor 98 in association with operation of the surgical instrument 10. In certain embodiments, the electric motor 98 may be activated through conventional electrical circuitry or components 102 that can be operatively associated with the firing trigger 38, the release button 40, and/or an independent manual activation switch 104 of the instrument 10. The electrical circuitry 102 may be configured to activate the motor 98 automatically in association with the firing operation of the instrument 10, for example; and/or to activate the motor 98 manually through use of the switch 104 which may be pressed by the clinician, for example, when using the instrument 10.

Figure 7:
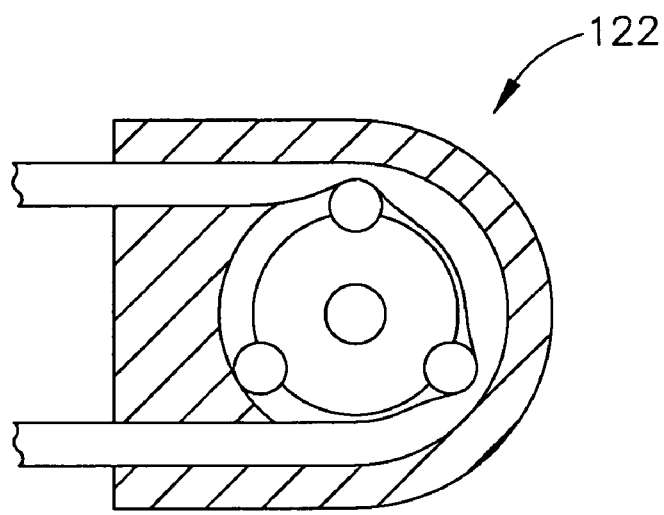
FIG. 7 includes a schematic of a pump that may be employed in accordance with various embodiments of the invention.
Figure 8:
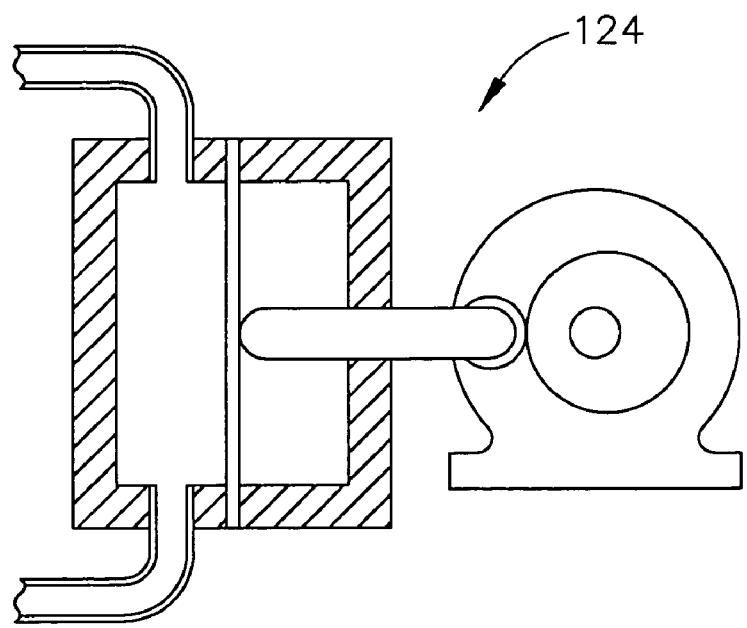
FIG. 8 includes a schematic of a pump that may be employed in accordance with various embodiments of the invention.

With reference to FIGS. 7 and 8, in various embodiments, the pump 100 may include, for example and without limitation, a peristaltic pump 122 (as shown in FIG. 7); a diaphragm pump 124 (as shown in FIG. 8); a rotary pump; or a variety of other types of pumps that may be suitably applied as the pump 100 in accordance with embodiments of the invention.

Figure 9:
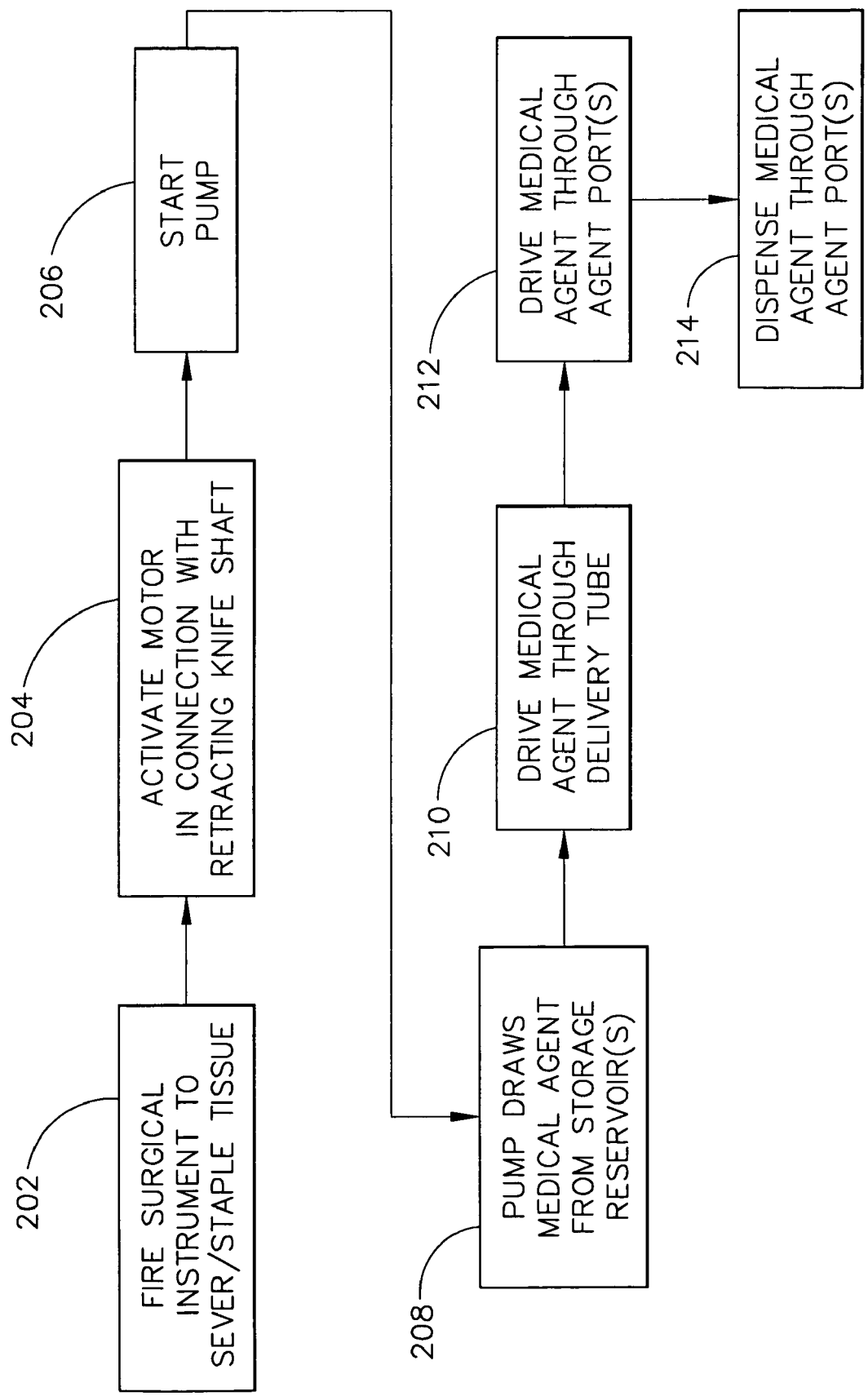
FIG. 9 includes a process flow diagram illustrating various aspects of an example of a method for using embodiments of the medical agent dispensing system of the present invention.
Figure 10:
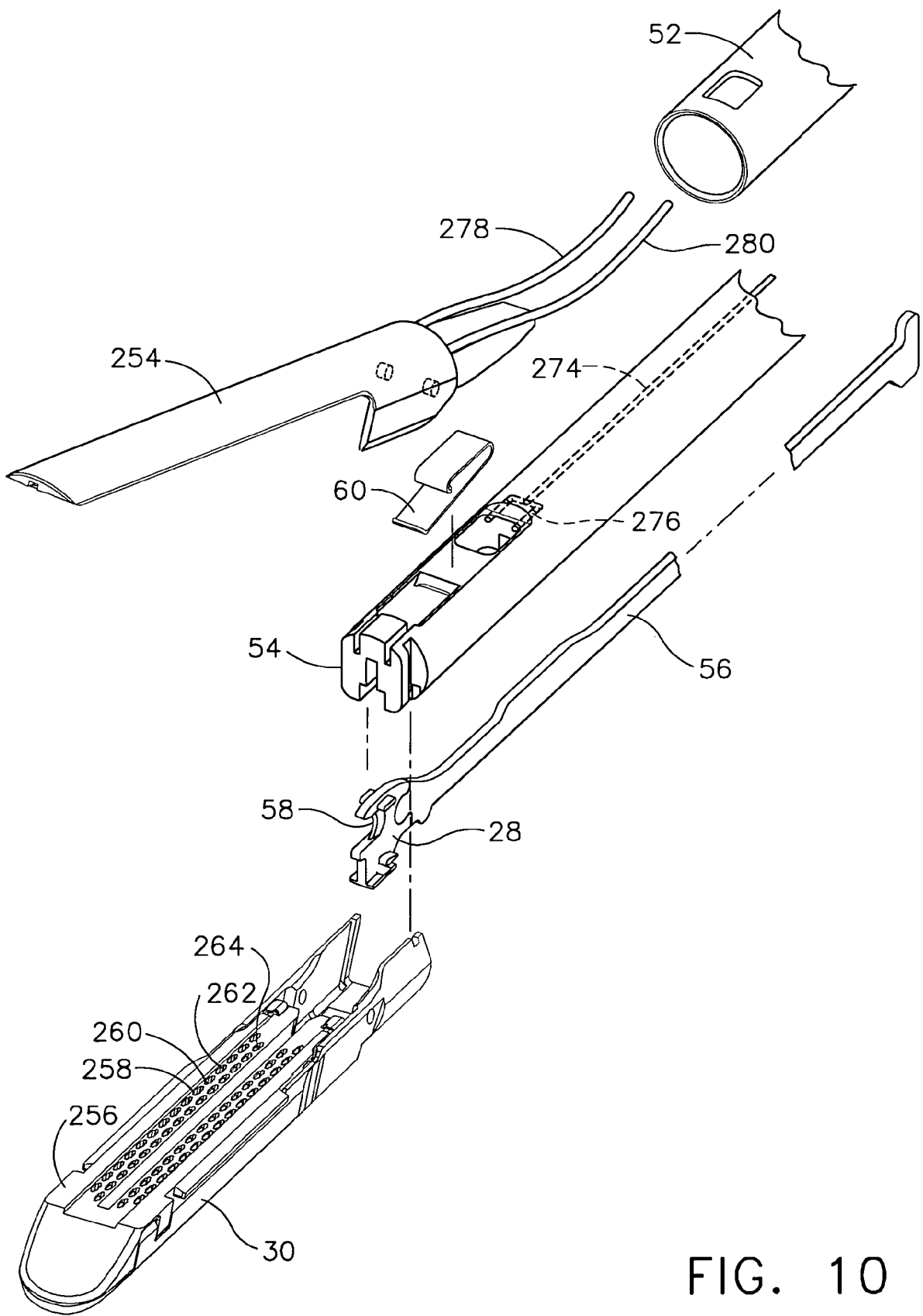
FIG. 10 illustrates a disassembled, three-dimensional view of the end effector and a shaft portion of a surgical instrument that may be configured in association with embodiments of a medical agent dispensing system of the present invention.

With reference to FIG. 9, a process flow diagram illustrates a method of applying the instrument 10 with various embodiments of the medical agent dispensing system in a surgical procedure performed on tissue. At step 202, the instrument 10 may be fired as described above to sever tissue and to apply staples to areas on both sides of an incision made in the tissue. At step 204, in connection with retraction of the knife shaft 56 from the severed/stapled tissue, the electric motor 98 may be activated to initiate rotation of the pump 100 at step 206. At step 208, the action of the pump 100 draws a quantity of a medical agent, or components combined to create a quantity of medical agent, from the storage reservoirs 92, 94 through the pump 100. At step 210, the medical agent is driven by the pump 100 through the delivery tube 72 (and associated tubing) to the lateral manifold 74. At step 212, the medical agent may be driven through the agent tubes 78, 80 to be dispensed at step 214 through the plurality of agent ports 82, 84, 86 formed in the staple cartridge 62. Once dispensed through the plurality of agent ports 82, 84, 86, the medical agent may then cover or deluge at least a portion of tissue areas severed/stapled by action of the instrument 10 at step 202.

With general reference to FIGS. 10 through 16, embodiments of the surgical severing/stapling instrument 10 may be structured with the closure tube 52 receiving and maintaining an end effector 26 including a modified anvil 254 and the channel 30. The channel 30 may be structured to removably receive a standard staple cartridge 256 therein. The staple cartridge 256 may have rows of multiple staple holes (such as illustratively representative staple holes 258, 260, 262, 264) formed therein and through which multiple staples (not shown) may be driven to staple severed tissue when the instrument 10 is fired. In certain embodiments, the staple cartridge 256 may be an "ETS45" or "ETS60" six-row cartridge, for example, marketed by Ethicon Endo-Surgery, Inc., of Cincinnati, Ohio. As shown more particularly in FIG. 11, the anvil 254 may include multiple rows of staple receiving depressions 266, 268, 270, 272 positioned in a corresponding relationship with the rows of staple holes 258, 260, 262, 264 of the staple cartridge 256. The multiple rows of staple depressions 266, 268, 270, 272 function to receive staples driven through the staple holes 258, 260, 262, 264 when the instrument 10 is fired to staple tissue.

Figure 11:
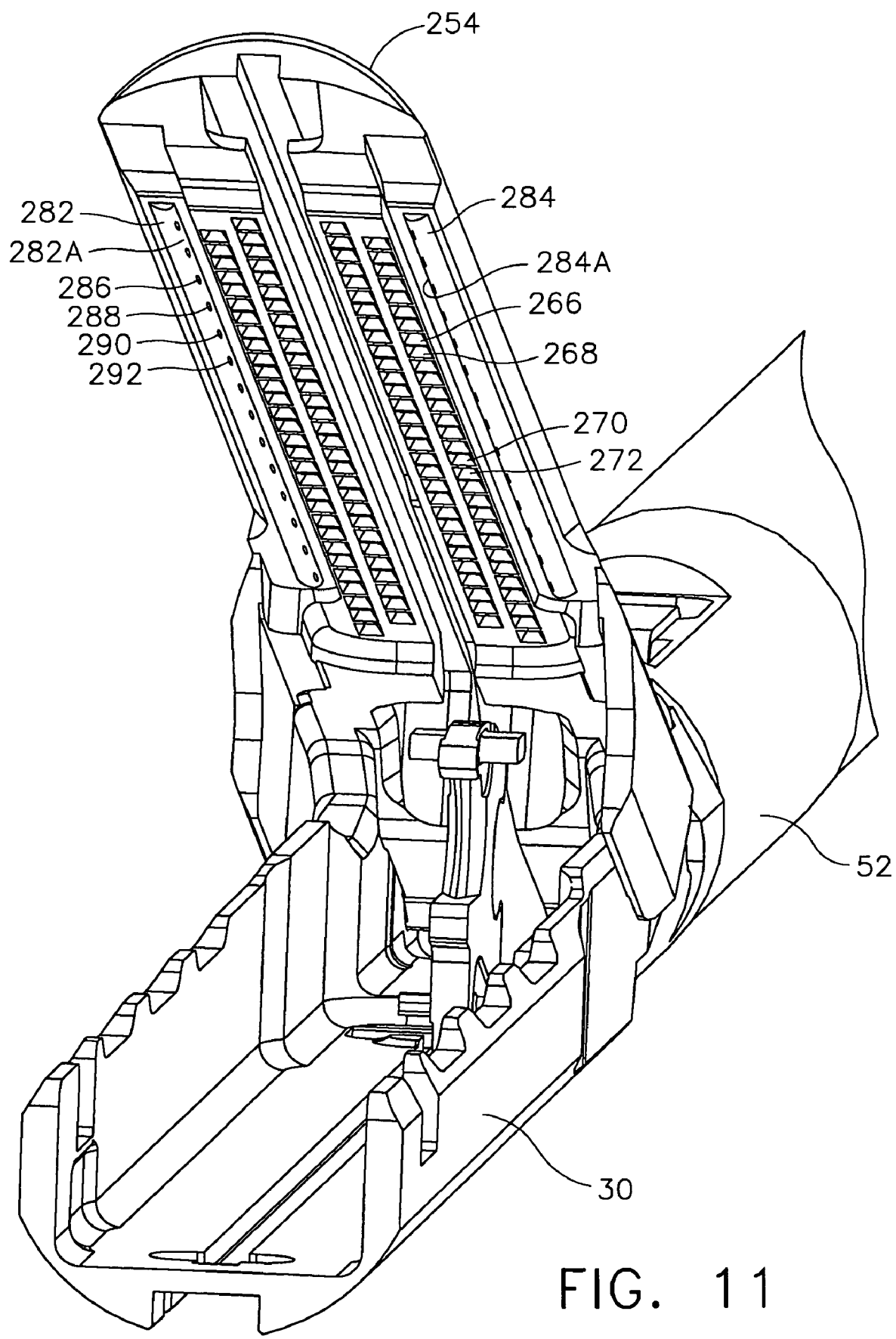
FIG. 11 includes an enlarged three-dimensional view of the end effector of the surgical instrument with the staple cartridge removed.
Figure 12:
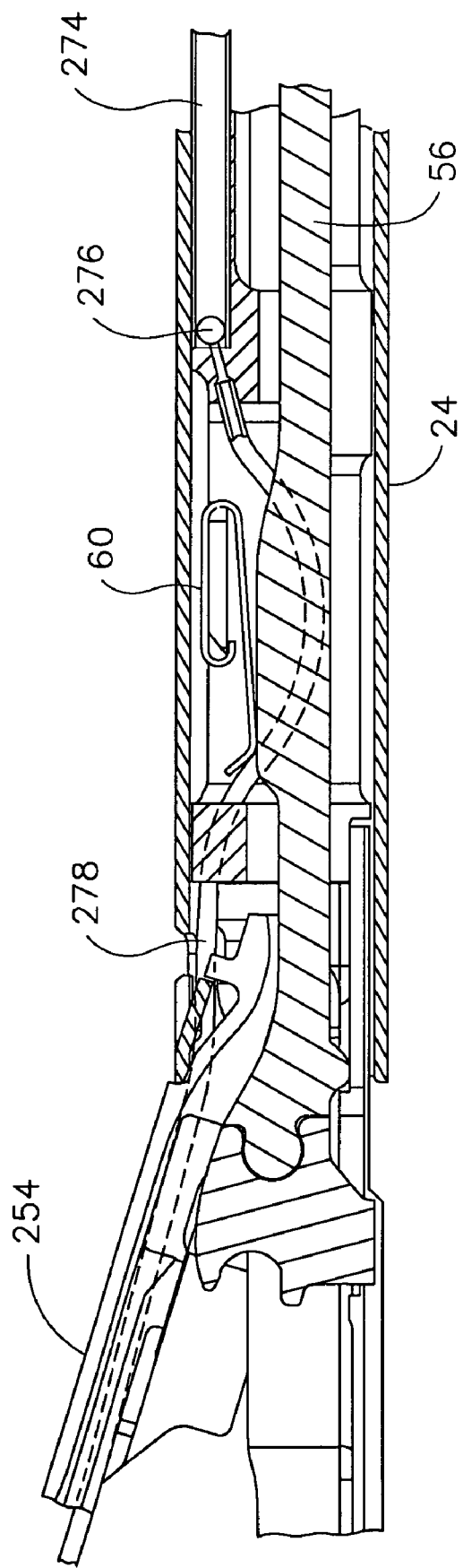
FIG. 12 includes a schematic view of certain portions of the shaft and end effector of the surgical instrument.
Figure 13:
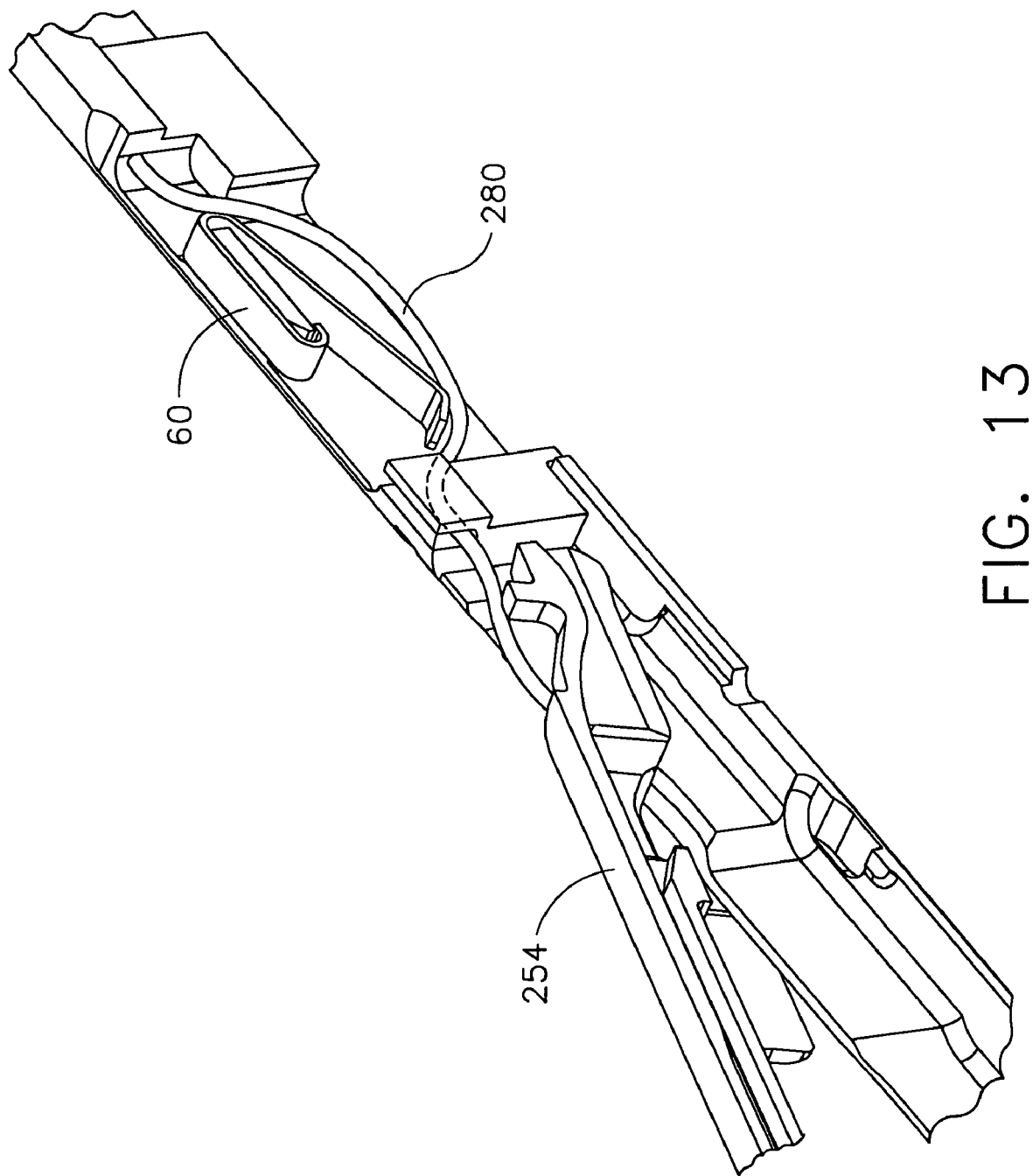
FIG. 13 includes a cut-away, three-dimensional view of certain portions of the shaft and end effector of the surgical instrument.
Figure 14:
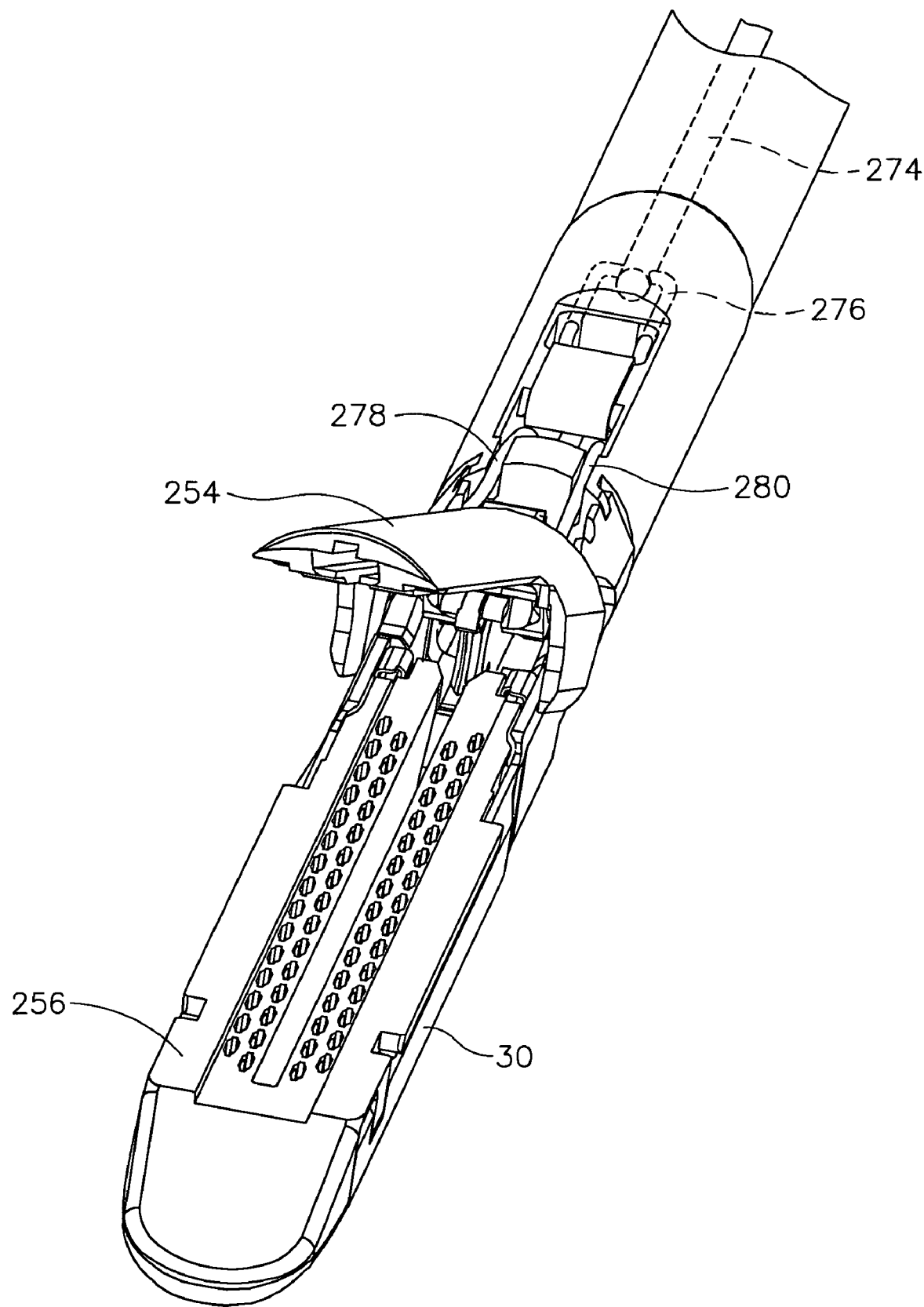
FIG. 14 includes a three-dimensional view of the end effector of the surgical instrument.
Figure 15:
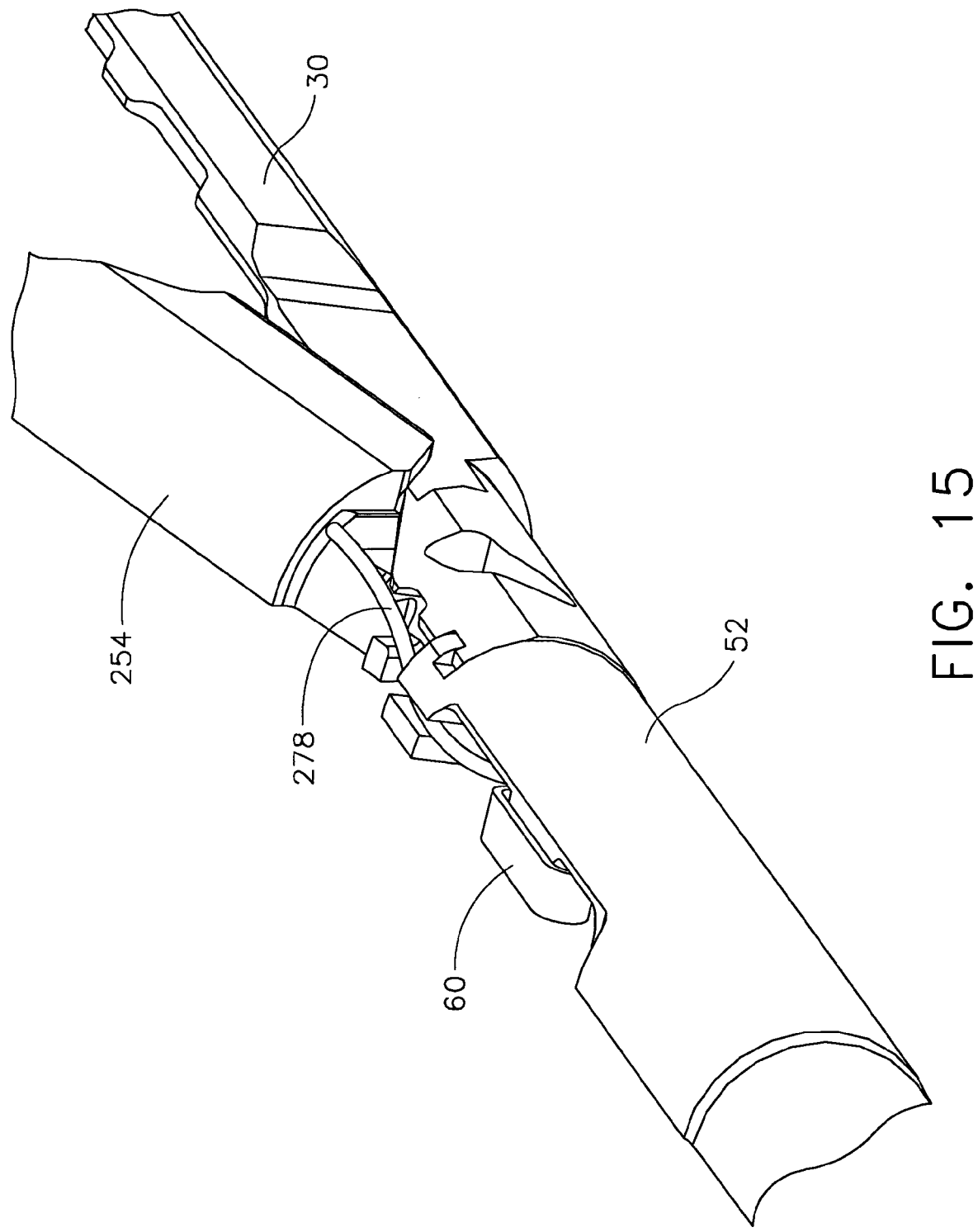
FIG. 15 includes a three-dimensional view of portions of the shaft and the end effector of the surgical instrument.

With regard to embodiments of a medical agent dispensing system that may be provided in conjunction with the surgical instrument 10, a delivery tube 274 may be positioned to extend longitudinally through the spine 54 to a lateral manifold 276. One or more agent tubes 278, 280 may be positioned to communicate with the lateral manifold 276 and with one or more agent port blocks 282, 284 (respectively) having a plurality of agent ports (such as illustratively representative agent ports 286, 288, 290, 292) formed therein. In general, FIGS. 12 through 15 illustrate the manner in which the agent tubes 278, 280 may be routed through the spine 54 to the anvil 254 of the instrument 10. As shown in FIG. 11, the agent port blocks 282, 284 may be connected to or formed on the anvil 254 generally adjacent to the rows of staple receiving depressions 266, 268, 270, 272 formed in the anvil 254. The agent ports 286, 288, 290, 292 may be formed on inner portions 282A, 284A of the agent port blocks 282, 284 to maximize the proximity of the agent ports 286, 288, 290, 292 to the staple receiving depressions 266, 268, 270, 272. It can be appreciated that the staple receiving depressions 266, 268, 270, 272 are proximate to severed/stapled tissue once the instrument 10 is fired. Thus, the positioning and sizing of the agent ports 286, 288, 290, 292 formed in the agent port blocks 282, 284 may be configured to maximize the portions of the severed/stapled tissue that can be covered or deluged by a medical agent delivered through the agent ports 286, 288, 290, 292 during operation of the instrument 10.

Figure 16:
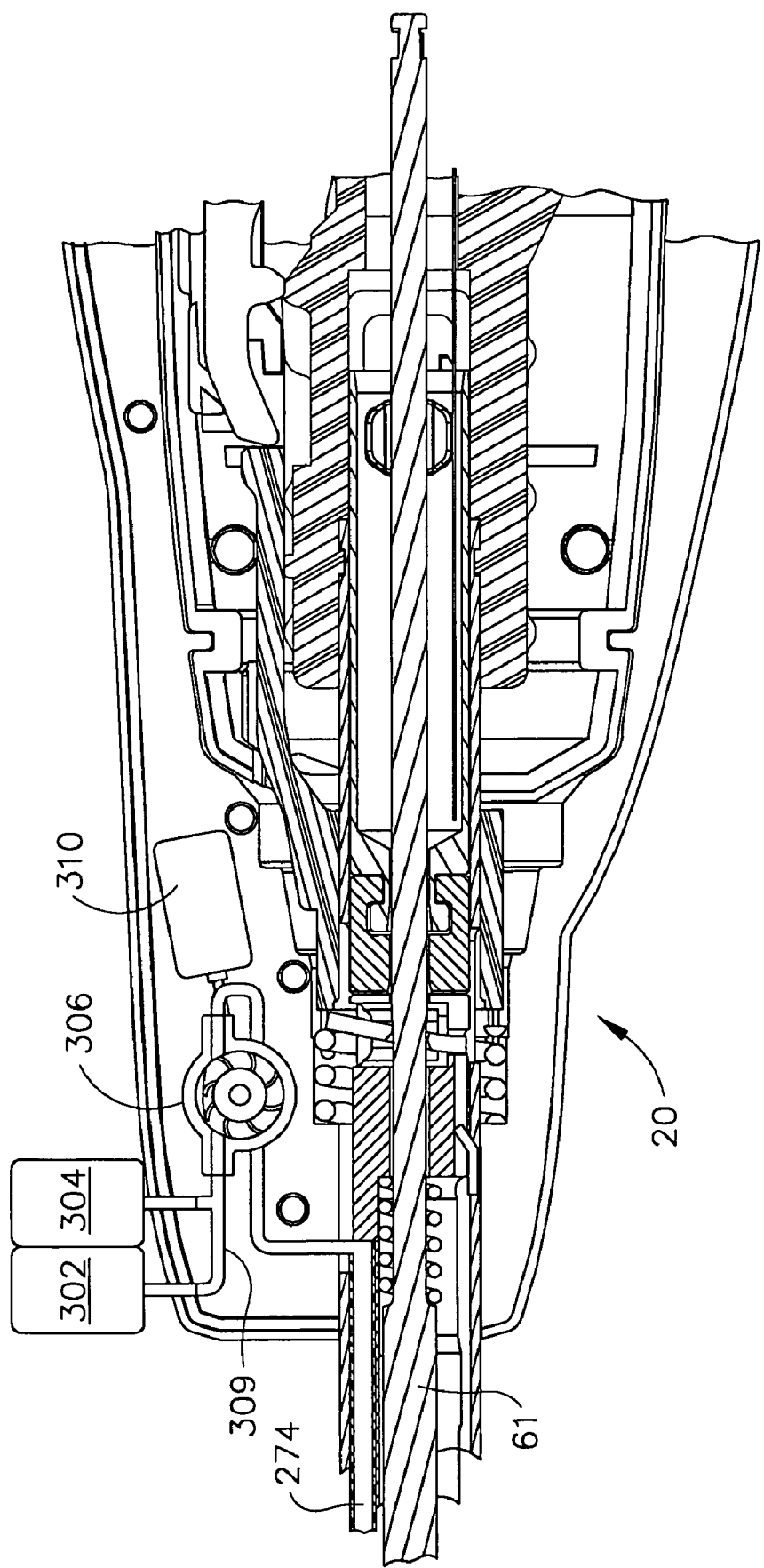
FIG. 16 includes a schematic of portions of the handle portion and the shaft of the surgical instrument; and, FIG. 17 includes a process flow diagram illustrating various aspects of an example of a method for using embodiments of the medical agent dispensing system of the present invention.

In various embodiments, the handle portion 20 of the instrument 10 may include one or more medical agent storage reservoirs 302, 304 mounted thereon and in communication with the delivery tube 274 through a pump 306. With particular reference to FIGS. 7, 8 and 16, the pump 306 may include, for example and without limitation, the peristaltic pump 122 (as shown in FIG. 7); the diaphragm pump 124 (as shown in FIG. 8); a rotary pump (as shown in FIG. 16); or a variety of other pumps that may be suitably applied in accordance with embodiments of the invention. The storage reservoirs 302, 304 may contain a variety of medical agents, or components thereof, that can be beneficially applied to severed and stapled tissue by the dispensing system in connection with use of the surgical instrument 10. While multiple storage reservoirs 302, 304 are depicted on the instrument 10 for convenience of disclosure, certain embodiments of the invention may employ only a single storage reservoir, for example, or more than two storage reservoirs. It can be seen that employing multiple storage reservoirs 302, 304 can facilitate real-time mixing of multiple-component medical agents during operation of the medical agent dispensing system. For example, one storage reservoir 302 may contain a first liquid and the other storage reservoir 304 may contain a second liquid. The first liquid may be the same kind of liquid as the second liquid, or the liquids may be different medical agents or components of medical agents. For example, multiple storage reservoirs 302, 304 can facilitate the use of two-part liquid adhesives designed to be combined during medical agent dispensing operations of the instrument 10. In operation, the medical agents stored in the storage reservoirs 302, 304 may be drawn to and driven through the delivery tube 274 by the action of the pump 306. The pump 306 may draw medical agents from the storage reservoirs 302, 304 through a reservoir manifold 309 in communication with the storage reservoirs 302, 304.

Also, in various embodiments of the medical agent dispensing system of the present invention, an electric motor 310 may be included within the handle portion 20 and operatively associated with the pump 306 to cause the pump 306 to draw medical agents from the storage reservoirs 302, 304. Those skilled in the art will appreciate that the electric motor 310 may be any conventional battery-driven or AC-powered motor provided with specifications (e.g., a motor rating) suitable for safe and effective use of the motor 310 in association with operation of the surgical instrument 10. In certain embodiments, the electric motor 310 may be activated as discussed above in association with the firing trigger 38, the release button 40, and/or the independent manual activation switch 104 of the instrument 10. In addition, as discussed above, the electrical circuitry 102 may be configured to activate the motor 310 automatically in association with the firing operation of the instrument 10, for example; and/or to activate the motor 310 manually through use of the switch 104 which may be pressed by the clinician, for example, when using the instrument 10.

Figure 17:
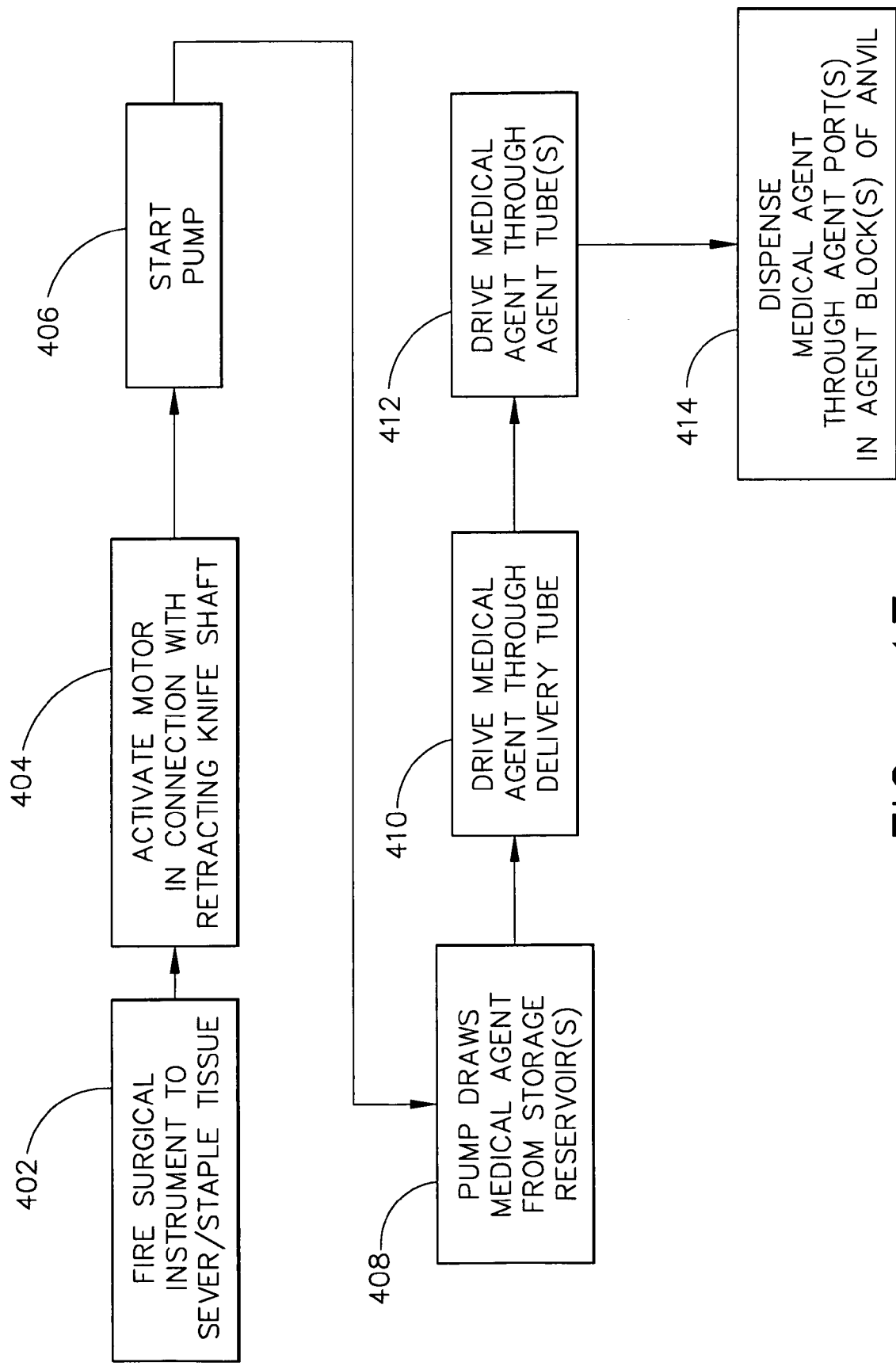

With reference to FIG. 17, a process flow diagram illustrates a method of applying the instrument 10 with various embodiments of the medical agent dispensing system in a surgical procedure performed on tissue. At step 402, the instrument 10 may be fired as described above to sever tissue and to apply staples to areas on both sides of an incision made in the tissue. At step 404, in connection with retraction of the knife shaft 56 from the severed/stapled tissue, the electric motor 310 may be activated to initiate the action of the pump 306 at step 406. At step 408, the pump 306 drives a quantity of a medical agent, or components combined to create a quantity of the medical agent, from the storage reservoirs 302, 304 through the pump 306 (and associated tubing). At step 410, the medical agent is driven and delivered through the delivery tube 274 to the lateral manifold 276 by the action of the pump 306. At step 412, the medical agent may be driven through the agent tubes 278, 280 to be dispensed at step 414 through the agent ports 286, 288, 290, 292 formed in the agent port blocks 282, 284 of the anvil 254. Once dispensed through the agent ports 286, 288, 290, 292, the medical agent may then cover or deluge at least a portion of tissue areas severed and stapled by action of the instrument 10 at step 402.

It will be appreciated that the terms "proximal" and "distal" may be used herein as convenient terms of relative orientation, such as with reference to a clinician gripping a handle of an instrument. For example, the end effector 26 may be considered "distal" with respect to the "proximal" handle portion 20 (see, e.g., FIG. 1). It will be further appreciated that, for convenience and clarity of disclosure, spatial terms of relative orientation such as "vertical" and "horizontal" or "downward" and "upward" may be used herein with respect to the drawings. Those skilled in the art will appreciate, however, that surgical instruments may be used in many orientations and positions, and such terms are not intended to be limiting and absolute.

Any patent, publication, or other disclosure material, in whole or in part, that is said to be incorporated by reference herein is done so only to the extent that the incorporated material does not conflict with existing definitions, statements, or other disclosure material set forth in the present disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The examples presented herein are intended to illustrate potential and specific implementations of the present invention for those skilled in the art. No particular aspect or aspects of the examples included herein are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable in a typical computer system or database system. However, because such elements are well known in the art and because they do not facilitate a better understanding of the present invention, a discussion of such elements may not be provided herein.

Any element expressed herein as a means for performing a specified function is intended to encompass any way of performing that function including, for example, a combination of elements that perform that function. Furthermore the invention, as defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments of the present invention disclosed herein, a single component may be replaced by multiple components, and multiple components may be replaced by a single component, to perform a given function or functions. Except where such substitution would not be operative to practice embodiments of the present invention, such substitution is within the scope of the present invention.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that surgical instruments structured in accordance with the present invention may find use in many surgical procedures, including but not limited to laparoscopic procedures and open procedures. Moreover, the unique and novel aspects of the embodiments of the present invention may find utility when used in connection with other forms of stapling apparatuses without departing from the spirit and scope of the present invention.

What is claimed is:

1. A surgical instrument, comprising:
    an actuator;
    an end effector comprising a movable member, wherein the movable member is configured to at least one of sever tissue and deploy staples from a staple cartridge; and
    a medical agent dispensing system, comprising:
        at least one storage reservoir structured for storing at least a component of a medical agent;
        a pump in communication with the storage reservoir, wherein the actuator is configured to operate the pump;
        a delivery tube in communication with the pump, the delivery tube being structured to receive a quantity of the medical agent from the storage reservoir during operation of the pump; and,
        at least one agent tube in communication with the delivery tube, the agent tube being structured for communication with at least one agent port formed in the staple cartridge of the surgical instrument for dispensing the medical agent therethrough.

2. The surgical instrument of claim 1, wherein the medical agent includes a hemostatic agent.

3. The surgical instrument of claim 1, wherein the medical agent includes an adhesive.

4. The surgical instrument of claim 1, wherein the pump is selected from the group consisting of a rotary pump, a peristaltic pump, or a diaphragm pump.

5. The surgical instrument of claim 1, wherein the delivery tube is in communication with the agent tube through a lateral manifold.

6. The surgical instrument of claim 5, wherein the agent tube is in communication with both the lateral manifold and a plurality of the agent ports.

7. The surgical instrument of claim 1, further comprising at least a second agent tube in communication with the delivery tube, wherein the first agent tube communicates with a first plurality of agent ports formed in the staple cartridge, and the second agent tube communicates with a second plurality of agent ports formed in the staple cartridge.

8. The surgical instrument of claim 1, further comprising at least one agent port being formed generally adjacent to at least one staple hole of the staple cartridge.

9. The surgical instrument of claim 1, further comprising at least a second storage reservoir in communication with the delivery tube, the second storage reservoir being structured for storing at least a component of the medical agent.

10. The surgical instrument of claim 9, wherein the component stored in the first storage reservoir and the component in the second storage reservoir are designed to be combined to form the medical agent.

11. The surgical instrument of claim 1, further comprising an electric motor configured to operate the pump.

12. A surgical instrument, comprising:
    an actuator;
    an end effector, comprising:
        a movable member configured to at least one of sever tissue and deploy staples from a staple cartridge; and
        an anvil; and
    a medical agent dispensing system, comprising:
        at least one storage reservoir structured for storing at least a component of a medical agent;
        a pump in communication with the storage reservoir, wherein the actuator is configured to operate the pump;
        a delivery tube in communication with the pump, the delivery tube being structured to receive a quantity of the medical agent from the storage reservoir during operation of the pump; and,
        at least one agent tube in communication with the delivery tube, the agent tube being structured for communication with at least one agent port formed in the anvil for dispensing the medical agent therethrough.

13. The surgical instrument of claim 12, wherein the medical agent includes at least one of a hemostatic agent or an adhesive.

14. The surgical instrument of claim 12, wherein the pump is selected from the group consisting of a rotary pump, a peristaltic pump, or a diaphragm pump.

15. The surgical instrument of claim 12, wherein the delivery tube is in communication with the agent tube through a lateral manifold.

16. The surgical instrument of claim 15, wherein the agent tube is in communication with both the lateral manifold and a plurality of the agent ports.

17. The surgical instrument of claim 12, further comprising at least a second agent tube in communication with the delivery tube, wherein the first agent tube communicates with a first plurality of agent ports formed in a first agent port block of the anvil, and the second agent tube communicates with a second plurality of agent ports formed in a second agent port block of the anvil.

18. The surgical instrument of claim 12, wherein the agent port is formed in an agent port block of the anvil.

19. The surgical instrument of claim 18, wherein the agent port is formed on a surface of the agent port block generally adjacent to at least one staple receiving depression formed in the anvil.

20. A surgical instrument comprising:
    a handle portion including at least one storage reservoir structured for storing at least a component of a medical agent, the handle portion further including a pump in communication with the storage reservoir;

a shaft portion connected to the handle portion, the shaft portion including a delivery tube in communication with the storage reservoir, such that a medical agent is deliverable from the storage reservoir to the delivery tube during operation of the pump;

an end effector operatively associated with the shaft portion, the end effector comprising:
  a channel configured to receive a staple cartridge; and
  a firing member configured to at least one of sever tissue and drive staples from the staple cartridge; and at least one agent tube in communication with the delivery tube, the agent tube extending from the shaft portion to communicate with at least one agent port formed in the staple cartridge for dispensing the medical agent therethrough.

21. The surgical instrument of claim 20, wherein the pump is selected from the group consisting of a rotary pump, a peristaltic pump, or a diaphragm pump.

22. A surgical instrument comprising:
a handle portion including at least one storage reservoir structured for storing at least a component of a medical agent, the handle portion further including a pump in communication with the storage reservoir;

a shaft portion connected to the handle portion, the shaft portion including a delivery tube in communication with the storage reservoir, such that a medical agent is deliverable from the storage reservoir to the delivery tube during operation of the pump;

an end effector operatively associated with the shaft portion, the end effector including:
  a firing member configured to at least one of sever tissue and drive staples from a staple cartridge; and
  an anvil; and at least one agent tube in communication with the delivery tube, the agent tube extending from the shaft portion to communicate with at least one agent port formed in the anvil for dispensing the medical agent therethrough.

23. The surgical instrument of claim 22, wherein the pump is selected from the group consisting of a rotary pump, a peristaltic pump, or a diaphragm pump.

* * * * *

UNITED STATES PATENT AND TRADEMARK OFFICE
CERTIFICATE OF CORRECTION

PATENT NO.       : 7,607,557 B2　　　　　　　　　　　　　　　　　　　　　Page 1 of 1
APPLICATION NO. : 11/267383
DATED            : October 27, 2009
INVENTOR(S)      : Shelton, IV et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 946 days.

Signed and Sealed this

Twelfth Day of October, 2010

David J. Kappos
*Director of the United States Patent and Trademark Office*